United States Patent
Kojima et al.

(10) Patent No.: US 7,910,284 B2
(45) Date of Patent: Mar. 22, 2011

(54) MATERIALS FOR PHOTORESIST, PHOTORESIST COMPOSITION AND METHOD OF FORMING RESIST PATTERN

(75) Inventors: Kyoko Kojima, Kunitachi (JP); Hideo Hada, Kawasaki (JP); Daiju Shiono, Kawasaki (JP)

(73) Assignees: Hitachi, Ltd., Tokyo (JP); Tokyo Ohka Kogyo Co., Ltd., Kanagawa-Ken (JP)

( * ) Notice: Subject to any disclaimer, the term of this patent is extended or adjusted under 35 U.S.C. 154(b) by 738 days.

(21) Appl. No.: 11/838,951

(22) Filed: Aug. 15, 2007

(65) Prior Publication Data
US 2008/0081281 A1    Apr. 3, 2008

(30) Foreign Application Priority Data
Sep. 29, 2006  (JP) ................. 2006-267830

(51) Int. Cl.
*G03F 7/004* (2006.01)
*G03F 7/30* (2006.01)
*C07C 63/00* (2006.01)
*C07C 43/23* (2006.01)

(52) U.S. Cl. .............. 430/270.1; 430/325; 430/905; 562/468; 568/640; 568/720

(58) Field of Classification Search ............. 430/270.1, 430/905, 910, 325
See application file for complete search history.

(56) References Cited

U.S. PATENT DOCUMENTS
| 7,659,047 B2 * | 2/2010 | Kojima et al. | ............ 430/270.1 |
| 2006/0105273 A1 | 5/2006 | Fukuda et al. | |
| 2007/0128541 A1 | 6/2007 | Kojima et al. | |
| 2008/0113294 A1 * | 5/2008 | Echigo et al. | ............ 430/270.1 |

FOREIGN PATENT DOCUMENTS
| JP | 2003-195502 | 7/2003 |
| WO | WO2004/012012 | 2/2004 |

OTHER PUBLICATIONS

Yukinori Ochiai, et al.; High-resolution, High-purity Calix[n]arene Electron Beam Resist; Journal of Photopolymer Science and Technology; 2000; pp. 413-417; vol. 13; No. 3.

Mitsuru Narithiro, et al.; 10-nm-Scale Pattern Delineation Using Calixarene Electron Beam Resist for Complementary Metal Oxide Semiconductor Gate Etching; Japanese Journal of Applied Physics; 2005; pp. 5581-5585; vol. 44; No. 7B.

* cited by examiner

*Primary Examiner* — John S Chu
(74) *Attorney, Agent, or Firm* — Antonelli, Terry, Stout & Kraus, LLP.

(57) ABSTRACT

To overcome the problem that a device performance is degraded by the edge roughness of a photoresist pattern, a mixture of polynuclear phenol compounds having, in one molecule, 0 to 6 functional groups which are chemically converted due to actions of an acid with the solubility in an alkaline developer reduced is used as a material for photoresist. In the mixture, two or more triphenyl methane structures are bonded to portions other than the functional group in the nonconjugated state. Furthermore, the mixture comprises polynuclear compounds with the average number of functional groups of 2.5 or below and includes the polynuclear compounds not having any functional group per molecule by 15% or less in the term of weight ratio, and the polynuclear phenol compounds having 3 or more functional groups per molecule by 40% or less.

7 Claims, 7 Drawing Sheets

FIG.1A

PAG-1

FIG.1B

PAG-2

FIG.1C

PAG-3

FIG.1D

PAG-4

FIG.1E

PAG-5

FIG.1F

PAG-6

FIG.1G

PAG-7

FIG.1H

PAG-8

FIG.1I

PAG-9

FIG.1J

PAG-10

FIG.1K

PAG-11

FIG.1L

PAG-12

FIG.2A

PAG-11

FIG.2B

PAG-12

FIG.2C

PAG-13

FIG.2D

PAG-14

FIG.2E

PAG-15

FIG.2F

PAG-16

FIG.2G

PAG-17

FIG.2H

PAG-18

FIG.2I

PAG-19

FIG.2J

PAG-20

FIG.2K

PAG-21

FIG.2L

PAG-22

FIG.2M

PAG-20

FIG.2N

PAG-21

FIG.2O

PAG-22

FIG.2P

PAG-23

MATERIALS FOR PHOTORESIST, PHOTORESIST COMPOSITION AND METHOD OF FORMING RESIST PATTERN

CLAIM OF PRIORITY

The present application claims priority from JP 2006-267830 filed on Sep. 29, 2006, the content of which is hereby incorporated by reference into this application.

BACKGROUND OF THE INVENTION

1. Field of the Invention

The present invention relates to negative-tone photoresist compositions used in extremely fine processing of a semiconductor device using extreme ultraviolet light (EUV light), materials for forming patterns used in the negative-tone resist compositions, and a method of patterns on a semiconductor device fabricated by using the negative-tone photoresist compositions.

2. Descriptions of the Related Arts

Nanofabrication by lithography using a photoresist is performed in a semiconductor device manufacturing process. In association with the recent tendency for a higher degree of circuit integration, fine patterns with the size less than 100 nanometers are often formed. A wavelength of beams or rays used for exposure has been increasingly reduced from that of a KrF excimer later beam (with the wavelength of 248 nm) to that of an ArF excimer laser beam (with the wavelength of 193 nm), and now the combination of the immersion exposure technique with ArF enables fabrication at the level of 100 nanometers or below. To realize nanofabrication at the level of 50 nanometers or below, the lithography technique using the extreme-ultraviolet rays (EUV light with the wavelength of 13.5 nm) or an electron beam is now under development. Now it is required to form various fine patterns including a hole pattern, an isolated line pattern, or a line-and-space, and therefore both positive-tone and negative-tone resist materials are required.

Another important factor which is important like the dimensions is processing accuracy, and it has been found that line edge roughness causes non-uniformity in pattern dimensions gives influences to performance of semiconductors.

To perform lithography, it is necessary to use a resist material based on a novolak resin or an acryl-based resin having the molecular weight of several thousands to several tens of thousands.

As the negative-tone resist material, the negative-tone resist for ArF described in JP-A-2003-195502 (Patent document 1) is well known. This resist has a hydrophilic γ-hydroxycarboxylic acid structure in a macromolecule side chain of the acrylic structure. In the exposed portion, intramolecular esterification occurs in the γ-hydroxycarboxylic acid moiety due to an effect of an acid generated from an acid generator, and the hydrophilic characteristic is changed to the hydrophobic one. Therefore, after development using an alkaline developer, the exposed portion becomes insoluble, and a negative-tone pattern is generated.

On the other hand, recently there are also research activities aiming at forming finer patterns not using macromolecules with the size of several nanometers or more, but using resist based on low-molecular-weight compounds with the size of 1 to 2 nanometers. A cross-linking type negative-tone resist using calixarene is reported in Journal of Photopolymer Science and Technology, 2000, 13, p. 413 (Non-patent document 1) and Japanese Journal of Applied Physics, 2005, 44, 7B, p. 5581 (Non-patent document 2. WO 2004/012012 Publication (Patent document 2) describes resist containing a non-polymer molecule as a main ingredient, and the molecule can provide high resolution and low LER, and has four or more reactive sites which are reactive moieties for the polarity-change reaction.

In the lithography process using a resist, it is required to improve the sensitivity from the view point of productivity.

SUMMARY OF THE INVENTION

When a resist composition based on a macromolecule is used, irregularities with the size at the order of several nanometers corresponding to the macromolecule size always appear on a side wall of a pattern, and the irregularity is referred to as LER.

In recent years, in association with the necessity of fabrication at increasingly smaller dimensions, the LER becomes relatively more visible, and achievement of required processing accuracy has become more and more difficult. For example, in the generation of hp45, the gate length is 20 nanometers or below, and the required processing accuracy is within 10% of the dimension. The nanofabrication as described above is actually impossible, because the resist material based on a macromolecule described in Patent document 1 include a large-size macromolecule as a main ingredient.

Furthermore, in the photo lithography or in the electron beam lithography, when a numerical aperture in a drawn portion becomes higher, a defect occurrence rate due to a foreign material disadvantageously becomes higher, and also in the electron beam lithography, there occurs the problem of lower throughput, so that also a negative-tone resist is required. Sensitivity of resist directly affect the throughput, and therefore high purity chemical amplification resist is desirable. The resist using calixarene described in Non-patent document 1 (Journal of Photopolymer Science and Technology, 2000, 13, p. 413-417) and Non-patent document 2 (Japanese Journal of Applied Physics, 2005, 44, 7B, p. 5581) provides high resolution and low LER, but the resist is of non-chemical amplification type, and therefore the sensitivity is low.

In a case of the resist using chloromethylated calixarene, development is performed with an organic solvent, and therefore there are the problems of toxicity and inflammability. There is also the problem that the resist can hardly be applied to a mass production line of semiconductors, because development is generally performed with an alkaline aqueous solution.

Patent document 2 (WO Publication 2004/012012) includes descriptions concerning a chemical amplification-based negative-tone resist using a low-molecular-weight compound and not causing increase in a molecular weight caused on lactonization which is an intra-molecular esterification reaction. This resist has four or more carboxyl groups per molecule, but the number of carboxyl group is large, sometimes carboxyl groups belonging to different molecules respectively form a stable dimer, which disadvantageously causes lactonization by acidic catalyst. Therefore, post exposure baking (PEB) at a high temperature is required for forming a pattern, and when PEB is performed at a high temperature, the diffusion length of an acid becomes larger, which disadvantageously lowers the resolution.

In a case of resist compositions based on low-molecular-weight compounds, those having about 6 phenolic hydroxy groups per molecule are excellent in the coating property, but it is impossible to introduce functional groups having a property as an acid catalyst involved in formation of negative-tone resist compositions only into a required number of phenolic hydroxy groups, and therefore the phenolic low-molecular-weight compounds used as raw materials remained in the product. When the residual ratio of raw materials is high, there occur the problems that the resolution disadvantageously lowers.

The present inventors found that the problems relating to the extremely fine processing of semiconductors and to the photoresist compositions used in the processing can be solved by using the materials for photoresist and the negative-tone photoresist compositions using the materials.

A configuration of the present invention is as described below.

A material for photoresist according to the present invention is expressed by chemical formula (1) below, and is a mixture of compounds having, in one molecule, zero to six functional groups which are chemically converted due to an action of an acid with the reduced solubility in an alkaline developer. The material has a structure in which two or more triphenyl methane structures are bonded in the nonconjugated state to a section other than the functional groups, and each of the functional groups is bonded to a phenolic hydroxy group of a polynuclear phenol compound (a), and a weight ratio of the polynuclear phenol compound (a) not having functional group per molecule is 15% or below, while a weight ratio of the polynuclear phenol compound (a) having three or more functional groups per molecule is 40% or below. Furthermore an average number of the functional groups in one molecule of the polynuclear phenol compound (a) is 2.5 or below.

Chemical formula (1)

In the formula above, Y denotes a functional group which is chemically converted due to action by a proton or an acid with the reduced solubility in an alkaline developer, and $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{26}$, and $R_{27}$ are a hydrogen atom or groups selected from the group consisting of a hydrocarbon and alkyl groups or aromatic hydrocarbon groups having 1 to 10 carbon atoms.

Resistance against dry etching and the capability of forming an amorphous film are required to photoresist materials based on the materials for photoresist according to the present invention, and therefore polynuclear compounds having high resistance against etching are used as the materials for photoresist.

A structure of a phenolic nuclear is defined as a unit structure equivalent to a structure of a phenol molecular expressed by chemical formula (5):

Chemical formula (5)

The polynuclear phenol is a compound having a plural phenolic nuclear structures in one molecule thereof. The polynuclear phenol compound has the problems that, when the molecular weight is too small, the volatility becomes disadvantageously high, and that, when the volatility is too high, an amorphous film cannot be formed. When the molecular weight is too large, there occurs the problem that size of the molecule is larger than LER. Therefore, a molecular weight of the polynuclear phenol compound is preferably in the range from about 500 to about 2500. Especially, the polynuclear phenol compound in which two or more triphenyl methane structures are bridged with the nonconjugated structure expressed by chemical formula (6) is advantageously used. In the chemical formula (6), $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ are a hydrogen atom or groups selected from the group consisting of a hydrocarbon and alkyl groups or aromatic hydrocarbon groups having 1 to 10 carbon atoms.

Specifically, a polynuclear phenol compound expressed by chemical formula (7) is advantageously used. The nonconjugated structure bonding a plurality of triphenyl methane structures to each other is preferably a straight or branched alkyl group such as methylene, ethylene, and propylene, or a fatty chain alkyl group.

Chemical formula (6)

Chemical formula (7)

3M6C-MBSA

25X-MBSA

26X-MBSA

The a functional group which is chemically converted due to action by a proton or an acid with the solubility in an alkaline developer included in the material for photoresist according to the present invention is a functional group which can be changed from the polar state to the not-polar state. A representative example of the polar group is preferably a γ- or δ-hydroxy carboxylic acid, and a representative example of the not-polar group is preferably γ- or δ-lactone generated when the polar group is esterified. Specifically, the γ-hydroxy carboxylic acid has the structure expressed by chemical formula (2). The δ-hydroxy carboxylic acid has the structure expressed by chemical formula (3).

Chemical formula (2)

Chemical formula (3)

In chemical formula (2) and chemical formula (3), each of $R_1$, $R_2$, $R_3$, $R_4$, $R_5$, $R_6$, $R_7$, and $R_8$ is a hydrogen atom or an alkyl group having 1 to 10 carbon atoms. Further any one of $R_1$, $R_2$, $R_3$, $R_4$, $R_5$, $R_6$, $R_7$, and $R_8$ is bonded to a hydroxyl group in the polynuclear phenol in the form of ether bond.

For bonding the γ- or δ-hydroxy carboxylic acid, which is a functional group chemically converted due to action by a hydrogen atom or an acid with the solubility in an alkaline developer to a hydroxyl group in the polynuclear phenol which is a material for photoresist according to the present invention, any of the structures expressed by chemical formulae (31) to '37) is used. In the formulae, $R_{31}$ to $R_{66}$ are alkyl groups having 1 to 6 carbon atoms.

Chemical formula (8)

The material for photoresist according to the present invention can be prepared through an etherification reaction between a polynuclear phenol compound having a structure in which 2 or more triphenyl methane structures are coupled in the nonconjugated structure and α-halo-γ-butyrolactone or -halo-δ-valerolactone (first step) and an alkaline hydrolysis reaction (second step). The etherification reaction in the first step can be performed by heating the reaction materials in an organic solvent such as diethyl ether, THF, or acetone and in the presence of a strong base such as sodium hydride, potassium hydride, sodium hydroxide, lithium hydroxide, sodium carbonate, or potassium carbonate. The alkaline hydrolysis reaction in the second step can be performed by dissolving the product from the first step in a solvent such as acetone, diethyl ether, THF, or 1,4-dioxane and adding a basic aqueous solution of sodium hydroxide, potassium hydroxide, sodium hydrogen carbonate, sodium carbonate, tetramethyl ammonium hydroxide, or tetraethyl ammonium hydroxide.

The etherification reaction performed for obtaining the materials for photoresist according to the present invention has low selectivity, and the reaction occurs at random in the probability to a plurality of hydroxyl groups in the polynuclear phenol compound used in the reaction, and therefore a plurality of products having different ratios respectively are obtained. On the other hand, an amount of a polar group introduced into the polynuclear phenol with the reduced solubility in an alkaline developer due to action by an acid (referred to an etherification ratio herein) is accessed by an average value of the products in the two-stage synthesis method described above, and the average value is preferably 3 or below because of the desired properties of the photoresist. More preferably the etherification ratio is in the rang from 1 to 2.5.

The reason is as described below. The first reason is that, when the etherification ratio is less than 1, there are large amount of the raw polynuclear phenol compounds, in which the solubility to an alkaline developer is not lowered due to actions of an acid and the etherification ration is substantially zero, and the sensitivity or resolution becomes disadvantageously lower. The second reason is that, when the etherification ratio is higher than 3, there are products with the functional groups (such as a carboxyl group) having high solubility in an alkaline developer, and therefore the development speed becomes excessively high. In this case, it is required to dilute the developer at a high ratio, or the sensitivity or the resolution lowers, which is disadvantageous. Therefore, it is preferable that the etherification ratio (the number of functional groups bonded to a polynuclear phenol compound) is in the range from 1 to 2.5 on average, and that a weight ratio of the compounds having the etherification ratio of zero is 15% or below and a weight ratio of the compounds having the etherification ratio of 3 or more is not more than 40%.

When, for instance, a polynuclear phenol 3M6C-MBSA is used as a raw material and etherification with α-bromo-γ-butyrolactone is performed, if the reaction is performed so that the etherification ratio is in the range from 1 to 2.5, the raw material with the etherification ratio of zero (3M6C-MBCA) is present in the total weight of the products by 20% or more, and also the products with the etherification ratio of 3 or more are present. To described in further details, the products obtained in the reaction condition for the etherification ratio of 1.0 (average value) includes the raw material with the etherification ratio of zero (3M6C-MBCA) by 36%. Furthermore, in the products obtained by accelerating the reaction under the condition for the etherification ratio of 2.2 (average value) for reducing a ratio of the raw material with the etherification ratio of zero, compounds with the etherification ratio of 3 or more are included by 34%. Therefore, it is understood that a ratio of the compounds with the etherification ratio of zero and the compounds with the etherification ratio of 3 or more cannot be lowered concurrently.

The present inventors found that a desired material for photoresist can be obtained by providing a step of separation and purification of a product of the etherification reaction between the first and second steps. Chromatography is employed in this separation step. The chromatography is a technique for separating various components mixed in a sample by moving the sample placed at an end of a solid phase (a solid or a liquid) in an appropriate eluent (moving phase) and separating the components from each other by making use of the moving speeds of the components reflecting differences in absorbability or distribution coefficient of the components. The column chromatography is preferably used, and in this technique, alumina or a silica gel, which is a solid phase, is filled in a vessel referred to as column, and separation of sample components is performed in a single or a mixed organic solvent such as toluene, xylene, heptane, diethyl ether, chloroform, butyl acetate. It is possible to reduce ratios of the compounds with the etherification ratio of zero and those with the etherification ratio of 3 or more from the products obtained in the first step for obtaining the materials for photoresist according to the present invention.

In the polynuclear phenol compound according to the present invention, the solubility of the compounds in an alkaline developer is reduced by the mechanisms shown by the chemical formula (9-1) or (9-2). Specifically, dehydration occurs between a carboxyl group and an alcoholic hydroxyl group in the same molecule to effect the intra-molecular esterification (lactonization). The functional group is converted from a polar structure promoting solubility in an alkalinene developer to a not-polar structure not promoting the solubility in an alkaline developer. Chemical formula 9 shows the representative example. In the other hydroxy carboxylic acid expressed by chemical formula (7), the dehydration between a carboxyl group and an alcoholic hydroxy group occurs. As a result, the solubility in an alkaline developer is reduced. At least one γ- or δ-hydroxy carboxylic acid structure is required for one molecule.

Chemical formula (9-1)

Chemical formula (9-2)

In the chemical formulae (9-1) and (9-2), $R_1$, $R_2$, $R_3$, $R_4$, $R_5$, $R_6$, $R_7$, and $R_8$ denotes a hydrogen atom or an alkyl group having 1 to 10 alkyl groups. Furthermore, any one of $R_1$, $R_2$, $R_3$, $R_4$, $R_5$, $R_6$, $R_7$, and $R_8$ is bonded to a hydroxy group in a polynuclear phenol by means of ether bond.

The material for photoresist according to the present invention can be used as a negative-tone resist composition by dissolving the material together with an acid generator, which generates an acid with irradiated by a radiation.

(Solvent)

The composition according to the present invention is dissolved in a solvent containing the components described above, and is applied onto a supporting body. The solvents, which can be used in the present invention, includes ethylene dichloride, cyclohexane, cyclopentanone, 2-heptanonw, γ-butyrolactone, methyl ethyl ketone, ethylene glycol monomethyl ether, ethylene glycol monomethyl ether, 2-methoxyethyl acetate, ethylene glycol monomethyl ether acetate, propylene glycol monomethyl ether, propylene glycol monomethyl ether acetate, propylene glycol monomethyl ether propionate, toluene, ethyl acetate, methyl lactate, ethyl lactate, methyl methoxypropionate, ethyl methoxypropionate, methyl pyruvate, ethyl pyruvate, propyl pyruvate, N,N-dimethyl formamide, dimethyl sulfoxide, N-methyl pyrrolidone, tetrahydrofuran, linear ketone having 6 to 9 carbon atoms, and δ-butyrolactone, and any of the solvents may be used singly or in combination with other one(s).

It is preferable to use, as an application solvent in the present invention, any of propylene glycol methyl ether acetate, propylene glycol monomethyl ether propionate, propylene glycol monomethyl ether, methyl lactate, ethyl lactate, linear ketone having 6 to 9 carbon atoms, and γ-butyrolactone, and the application solvents provide excellent in-plane uniformity. The linear ketone having 6 to 9 carbon atoms includes 2-heptanone, 2-octanone, and the like.

The photoresist composition according to the present invention is dissolved in a solvent, and then is preferably filtered to remove insoluble materials. The filter used in the process is selected from generally used in the field of photoresist.

(Acid-Generator)

Any compound may be used as a photo-acid generator used in the photoresist composition according to the present invention on the condition that the compound generates an acid when irradiated by an electron beam, ultraviolet rays, X-ray, or the like.

Specifically, the compound is selected from onium salt compounds (sulfonium salt compounds, iodonium salt compounds), sulfonium imide compounds, sulfonium methyde compounds, organic halide compounds, sulfonic acid ester compounds, sulfonate compounds, and the like as shown in FIG. 1A-1L and FIG. 2A-2P. One or more photoresist compositions selected from those listed above may be used in the photoresist composition according to the present invention singly or in combination.

A content of the photo-acid generator in the photoresist composition according to the present invention as expressed with a weigh ratio of the photo-acid generator against the photoresist composition is in the range from 1% to 30%, and more preferably in the range from 5% to 20%. When a content of the photo-acid generator is too small, there occurs the problem that the sensitivity is low, or that patterning cannot be performed. When a content of the photo-acid generator is too large, there occur the problems, for example, that formed patterns degrade, that the line edge roughness increases, and that the resolution becomes lower.

(Basic Compound)

A basic quencher compound may be added in the negative-tone resist composition according to the present invention for the purpose to improve the resolution. For the purpose, there is generally known the technique of irradiating a radiation to a desired pattern on a resist-applied film so that the acid component generated due to irradiation of radiation is diffused in the resist film during the subsequent baking step for a chemically amplifying reaction. In the negative-tone resist, the diffusion of the quencher compound is observed as a distribution of the acid component. By neutralizing the acid diffused in response to addition of the basic quencher compound, the deformation of patterns as described above can be suppressed, and as a result resolution of the resist is improved.

The basic quencher compound which may be used in the present invention should be more basic as compared to phenols. A nitrogen-containing basic compound is especially preferable. The structures shown in FIG. 3A to 3E are examples of preferable compounds.

In the chemical formulas shown in the figure, $R_{1250}$, $R_{1251}$, and $R_{1252}$ are identical to or different from each other, and are hydrogen atom, an alkyl group having 1 to 6 carbon atoms, amino alkyl group having 1 to 6 carbon atoms, a hydroxy alkyl group having 1 to 6 carbon atoms, or a substituted or not-substituted aryl group having 6 to 20 carbon atoms. $R_{1251}$ and $R_{1252}$ may be bonded to each other to form a ring. In the chemical formulas, $R_{1253}$, $R_{1254}$, $R_{1255}$, and $R_{1256}$ may be identical to or different from each other, and denote alkyl groups each having 1 to 6 carbon atoms respectively. Preferable examples include substituted or not-substituted guanidine, substituted or not-substituted amino pyridine, substituted or not-substituted amino alkyl pyridine, substituted or not substituted amino pyrrolidine, substituted or not-substituted imidazole, substituted or not substituted pyrazole, substituted or not-substituted pyridine, substituted or not-substituted pyrimidine, substituted or not-substituted purine, substituted or not-substituted substituted imidazolyn, pyrazoline, substituted or not-substituted substituted piperazine, substituted or not-substituted amino morpholyne, and substituted or not-substituted amino alkyl morpholyne. Especially preferable compounds include, but not limited to, guanidine, 1,1-dimethyl guanidine, 1,1,3,3-tetramethyl guanidine, 2-amino pyridine, 3-amino pyridine, 4-phenyl pyridine, 4-amino pyridine, 2-dimethylamino pyridine, 4-dimethylamino pyridine, 2-diethylamino pyridine, 2-(amino methyl) pyridine, 2-amino-3-methyl pyridine, 2-amino-4-methyl pyridine, 2-amino-5-methyl pyridine, 2-amino-6-methyl pyridine, 3-aminoethyl pyridine, 4-aminoethyl pyridine, 3-amino pyrrolydine, piperazine, N-(2-aminoethyl)piperazine, N-(2-aminoethyl)pyperidine, 4-amino-2,2,6,6-tetramethyl pyperidine, 4-piperidino-pyperidine, 2-iminopiperidine, 1-(2-aminoethyl)pyrrolydine, pyrazole, 3-amino-5-methyl pyrazole, 5-amino-3-methyl-1-p-tolylpyrazole, pyrazine, 2-(aminomethyl)-5-methyl pyrazine, pyrimidine, 2,4-diamino pyrimidine, 4,6-dihydroxy pyrimidine, 2-pyrazoline, 3-pyrazoline, N-amino morpholyn, N-(2-aminoethyl) morpholyn, 1,8-diazabicyclo [5,4,0] undeca-7-en, 1,5-diazabicyclo[4,3,0] nona-5-en, and 2,4,5-triphenyl imidazole.

The nitrogen-containing basic compounds may be used singly or in combination. A use rate of the nitrogen-containing basic compound against all of the components of the composition according to the present invention should be in the range from 0.001 to 10 weight %, and is preferably in the range from 0.01 to 2 weight %. When the content is less than 0.001 weight %, the effect of addition of the composition cannot be obtained. On the other hand, when the content is more than 2 weight %, there occurs that the sensitivity lowers or that the resolution in a not-exposed section becomes disadvantageously lower.

(Surfactant)

In addition, it is preferable in the present invention to use a fluorine-based and/or silicon-based surfactant. The fluorine-based and/or silicon-based surfactant includes a fluorine-based surfactant, a silicon-based surfactant, and a surfactant containing both a fluorine atom and a silicon atom.

Specifically, the fluorine-based surfactants or silicon-based surfactants available in the present invention include F-top EF301, EF303 (produced by Shin Akita Kasei (K. K.)), Fluorad FC430, 431 (produced by Sumitomo 3M Co. Ltd), Megafac F171, F173, F176, F189, F08 (produced by DAINIPPON INK AND CHEMICALS INCORPORATED), Surflon S-382, SC-101, 102, 103, 104, 105, 106 (Produced by Asahi Glass Co., Ltd.), Troysol S-366 (Tryo Chemicals Co. Ltd.). Furthermore, also polysiloxane polymer KP-341 (produced by Shin-Etsu Chemical CO., Ltd.) can be used as a silicon-based surfactant. A blending quantity of the surface surfactant relative to a solid content of all compositions in the composition according to the present invention is generally in the range from 0.001 to 0.5 weight %, and more preferably in the range from 0.002 to 0.1 weight %. Surfactants other than the fluorine-based and/or silicon-based surfactants may be used in the present invention.

Specifically, the other type of surfactants which can be used in the present invention include nonion-based surfactants including polyoxyethylene alkyl ethers such as polyoxyethylene lauryl ether, polyoxyethylene stearyl ether, polyoxyethylene cetyl ether, polyoxyethylene oleyl ether; polyoxyethylene alkylallyl ether such as polyoxyethylene octylphenol ether, and polyoxyethylene nonylphenol ether; polyoxyethylene propylene block copolymer; sorbitan fatty acid esters such as sorbitan monolaurate, sorbitan monopalmitate, sorbitan monostearate, sorbitan monooleate, sorbitan trioleate, and sorbitan tristearate; polyoxyethylene sorbitan fatty acid esters such as polyoxyethylene sorbitan laurate, polyoxyethylene sorbitan palmitate, polyoxyethylene sorbitan monostearate, polyoxyethylene sorbitan trioleate, polyoxyethylene sorbitan tristearate. Also crylic acid-based or methacrylic acid-based (co)polymerized Polyflow No. 75, No. 95 (produced by Kyoueisha Fatty Chemical Industry Co. Ltd.) may be used for this purpose. A blending quantity of the other type of surfactant relative to all of the solid components in the composition according to the present invention is generally 2 weight % or below, and more preferably 0.5 weight % or below. These surfactants may be used singly or in combination.

Effects provided by addition of a surfactant include improvement in compatibility between the photoresist composition according to the present invention and a photo-acid generator and reduction in irregularities on an applied surface.

A method of forming resist patterns using the negative-tone photoresist composition according to the present invention comprises a step of applying the negative-tone resist composition on a matrix to obtain a resist layer, a step of irradiating a radiative ray to the resist layer, and a step of developing the resist layer irradiated by the radiation. As the radiation, the ArF laser light (with the wavelength of 193 nm), EUV light (with the wavelength of 13.5 nm), or X-ray may be used. The acid-generator is preferable sensitive to the radiation irradiated to the resist layer.

As the developer for the composition of the present invention, it is possible to use an alkaline aqueous solution of any of the following compounds; inorganic alkalis such as sodium hydroxide, potassium hydroxide, sodium carbonate; primary amines such as ethylamine, and n-propylamine; ammonia water; secondary amines such as diethylamine, di-n-butylamine; tertiary amines such as triethylamine, and methyl diethyl amine; alcohol amines such as dimethylethanolamine, and triethanolamine; quarternary ammonium salts such as tetramethyl ammonium hydroxide, and tetraethyl ammonium hydroxide; and cyclic amines such as pyrrole, and pyperidine. Furthermore, an appropriate quantity of alcohols or a surfactant may be added in the alkaline aqueous solution. It is preferable to use an aqueous solution of tetramethyl ammonium hydroxide with the concentration in the range from 0.05 to 10 weight %. When the concentration is less than 0.05%, the resist film is not dissolved. When the concentration is 10% or more, sensitivity of the resist remarkably may drop, a form of prepared pattern may degrade, or any pattern may not be formed.

With the configuration as described above, it is possible to provide a negative-tone photoresist material well suited to the EB lithography or the EUV lithography and having high sensitivity, high resolution, and low line edge roughness, and a method of resist formation using the material.

DETAILED DESCRIPTION OF THE PREFERRED EMBODIMENT

Embodiments of the present invention are described in detail below, but the present invention is not limited to the embodiments.

First Embodiment

In a first embodiment, a method of obtaining materials for photoresist (A1, A2, and A3) by column chromatography according to the present invention is described.

In a first step (for an etherification), polynuclear phenolic compound 3M6C-MBSA (15 g) and potassium carbonate (7 g) were added to acetone (300 ml), and the mixture was sufficiently stirred. Then a solution prepared by adding a-bromo-γ-butylolactone (4.0 g) in acetone solution (50 ml) was added to the mixture at the room temperature, and the mixed solution was stirred for two hours at the temperature of 45 degrees C. After the reaction is completed, acetone was removed from the solution by evapolation under the reduced pressure, water (250 ml) and ethyl acetate (205 ml) were added to the solution, and the solution was sufficiently shaken in 1 L separating funnel. An organic layer was recovered, washed with water (300 ml), concentrated, vacuum-dried, and polynuclear phenolic compound (17 g) was obtained. High-performance liquid chromatography (HPLC) analysis was performed to find that the etherification rate is 1.1 per molecule on average, and specifically, a percentage of compounds having the etherification rate of 1 was 33%, a percentage of compounds having the etherification rate of 2 was 20%, a percentage of compounds having the etherification rate of 3 was 7%, and a percentage of compounds having the etherification rate of 4 was 2%.

Figure 1A:
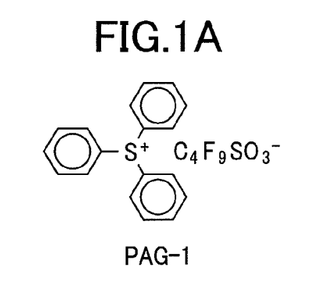
FIG. 1A-1L are views illustrating a chemical formula of an acid generator used in an embodiment of the present invention.
Figure 1B:
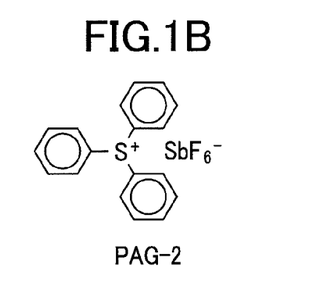
Figure 1C:
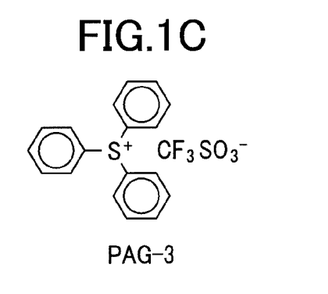
Figure 1D:
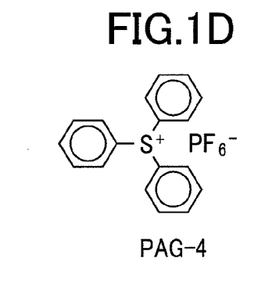
Figure 1E:
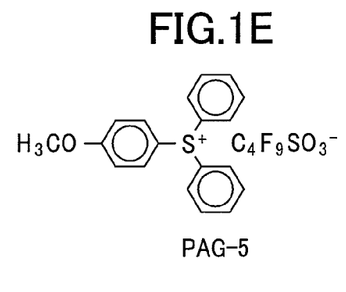
Figure 1F:
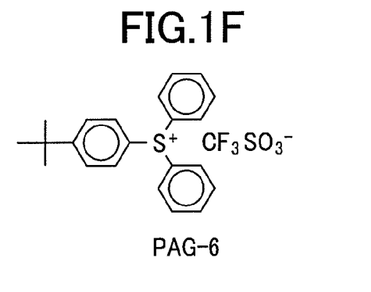
Figure 1G:
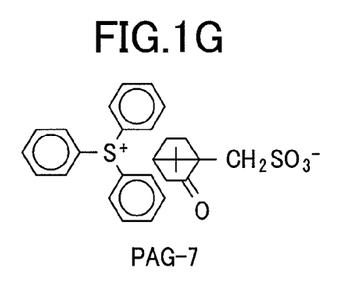
Figure 1H:
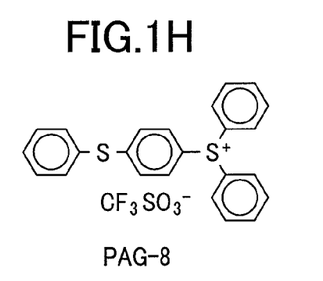
Figure 1I:
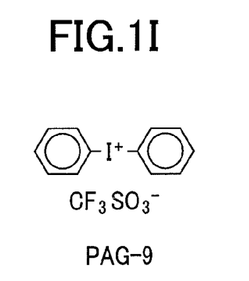
Figure 1J:
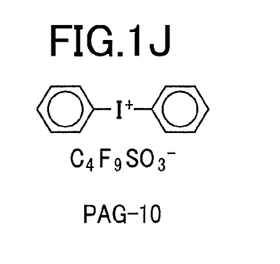
Figure 1K:
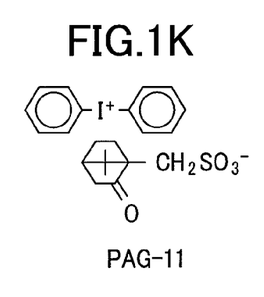
Figure 1L:
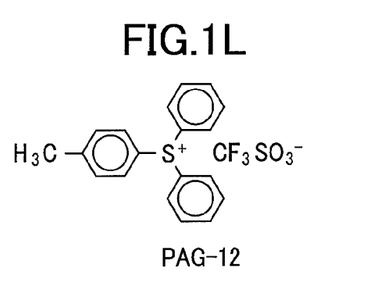
Figure 2A:
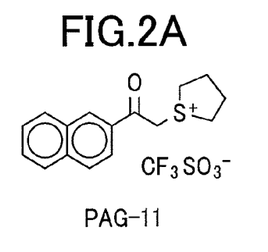
FIG. 2A-2P are views illustrating a chemical formula of an acid generator used in an embodiment of the present invention.
Figure 2B:
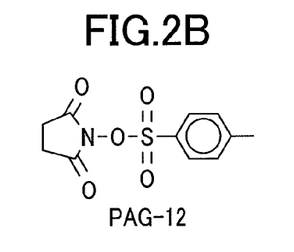
Figure 2C:
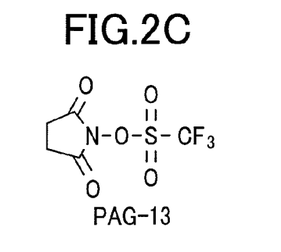
Figure 2D:
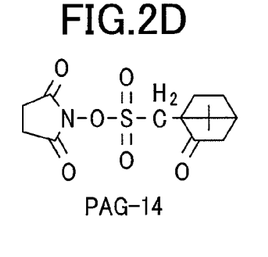
Figure 2E:
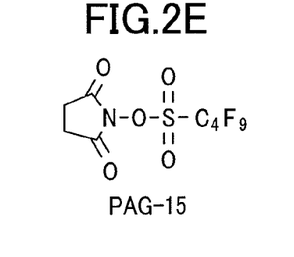
Figure 2F:
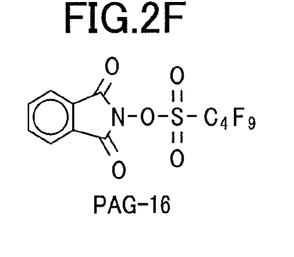
Figure 2G:
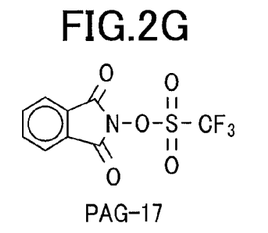
Figure 2H:
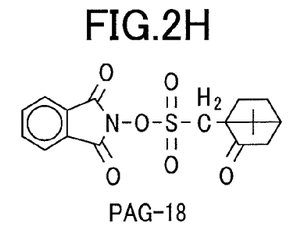
Figure 2I:
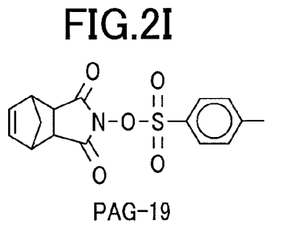
Figure 2J:
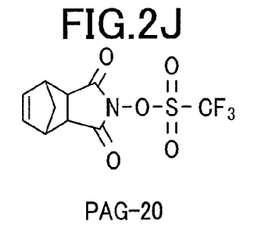
Figure 2K:
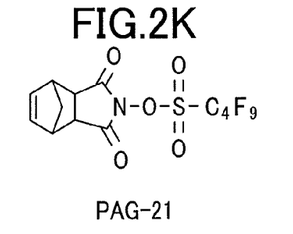
Figure 2L:
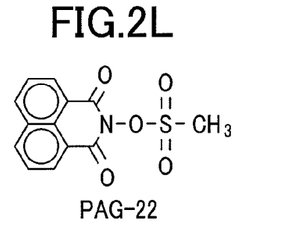
Figure 2M:
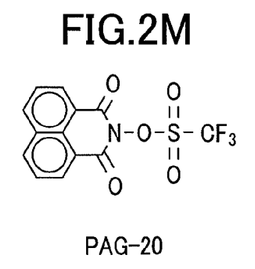
Figure 2N:
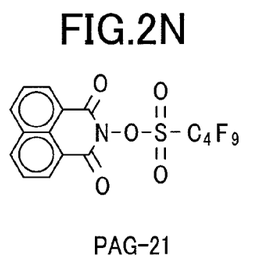
Figure 2O:
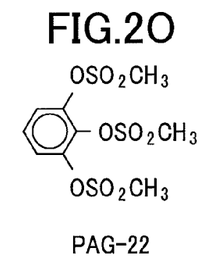
Figure 2P:
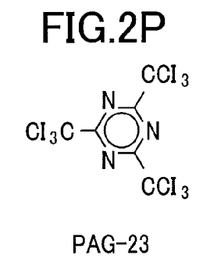
Figure 3A:
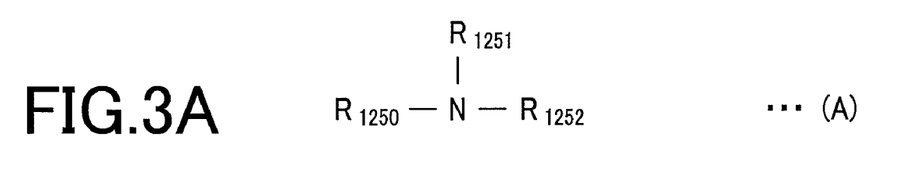
FIG. 3A-3E are views illustrating a chemical formula of a basic compound used in an embodiment of the present invention.
Figure 3B:
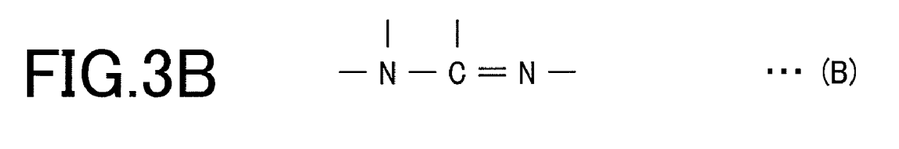
Figure 3C:
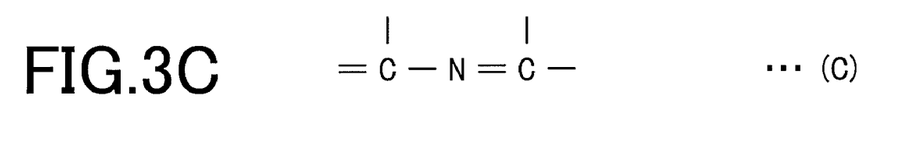
Figure 3D:
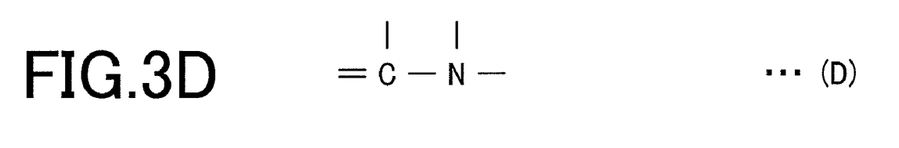
Figure 3E:
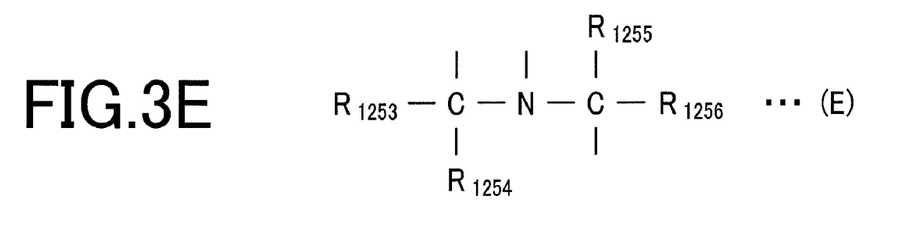
Figure 4:
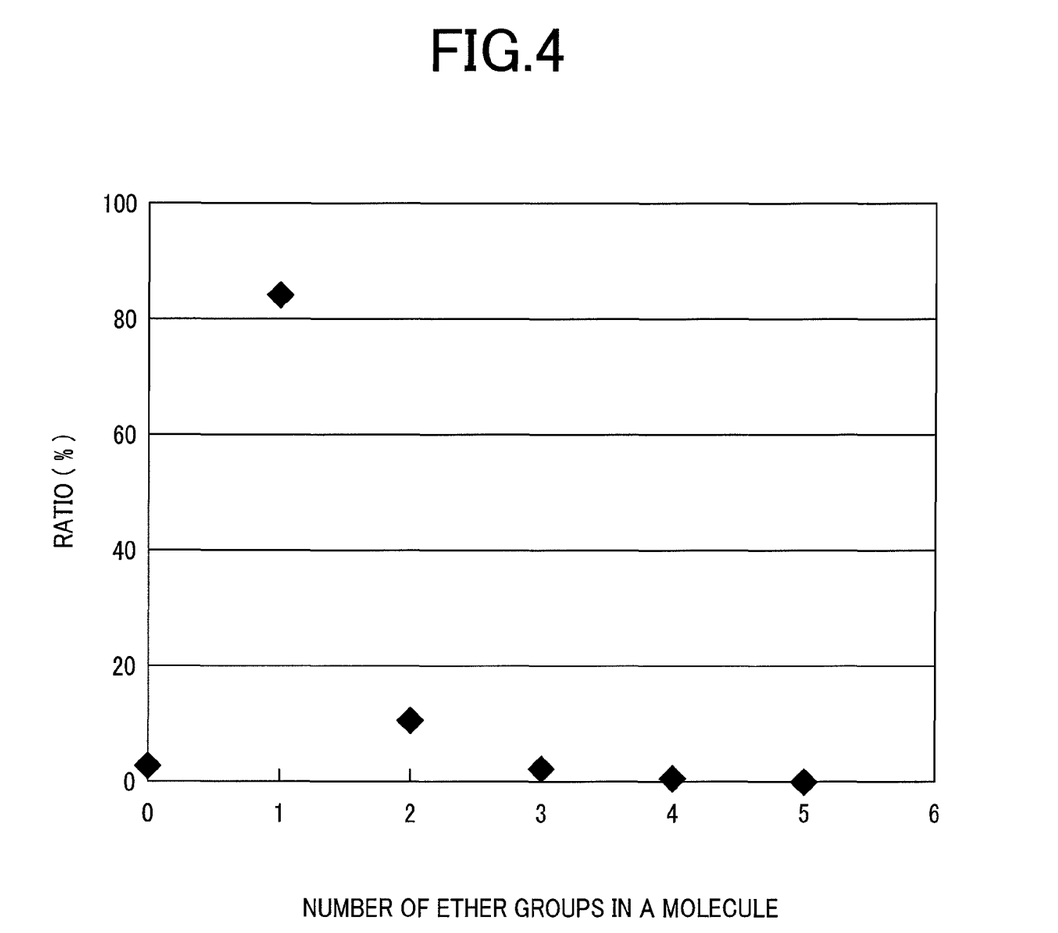
FIG. 4 is a view illustrating a composition distribution of a material for photoresist A1 after column chromatography.

In a step for separation and refinement by the column chromatography, the resultant compound in the first step was dissolved into ethyl acetate (20 ml), and the compound was separated by the column chromatography, with silica gel as a bonded phase and a mixed solvent including diethyl ether and ethyl acetate as an extraction solvent. The eluate was isolated by 20 ml, and compositions of the recoverable compounds for each fraction were analyzed by HPLC. An appropriate quantity of each fraction was recovered, the solvent was removed by concentration and vacuum-dried, and etherified compound of the polynuclear phenol 3M6C-MBSA (6 g) was obtained, the composition of which is shown in FIG. 4. The etherification rate is 1.1 on average, and specifically, a percentage of compounds having the etherification rate of 0 was 2.5%, a percentage of compounds having the etherification rate of 1 was 85%, a percentage of compounds having the etherification rate of 2 was 10%, and a percentage of compounds having the etherification rate of 3 was 2.5%.

Figure 7:
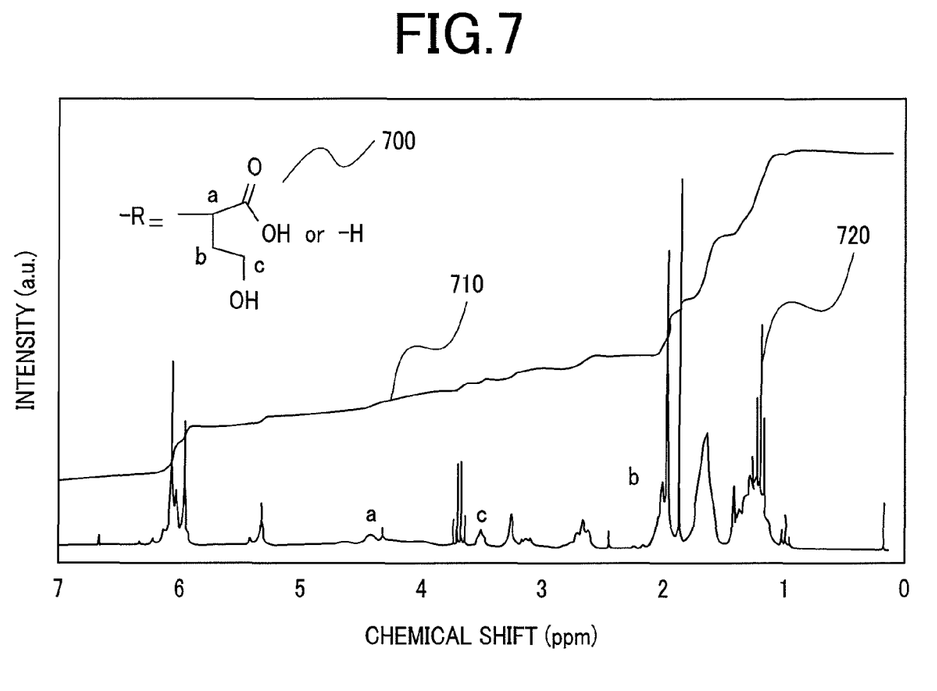
FIG. 7 is a view illustrating a 1H-NMR spectrum of the material for photoresist A1.

In a second step (for alkaline hydrolysis), the ether compound of the polynuclear phenol 3M6C-MNSA (6 g) which was separated and purified by the column chromatography was dissolved in THF (100 ml). TMAH aqueous solution was added to the resultant solution, until pH of the solution was adjusted to 2.38%. The solution was stirred for 2 hours at the room temperature, THF was removed by evapolation under the reduced pressure, ethyl acetate (200 ml) was added, 1% of hydrochloric acid was added until the pH was adjusted to about 5, while stirring vigorously. The organic layer was washed with water and saturated NaCl aqueous solution, dried with sodium sulfate, concentrated, and a material for photoresist A1 (5.4 g) was obtained. The number of introduced γ-hydroxycarboxylic acid groups calculated by HPLC was identical to the etherification rate calculated after the step for the separation and purification, because no ether bond decomposition occurs in this step. FIG. 7 illustrates 1H-NMR spectrum of A1, and the signs a, b, and c denotes the spectrum assignment for the γ-hydroxycarboxylic groups. The protons were 1 to 1.4 ppm for the methyl group, 1.6 to 1.8 ppm for the cyclohexyl group, and 6.6 to 7.0 ppm for the benzene ring.

Figure 8:
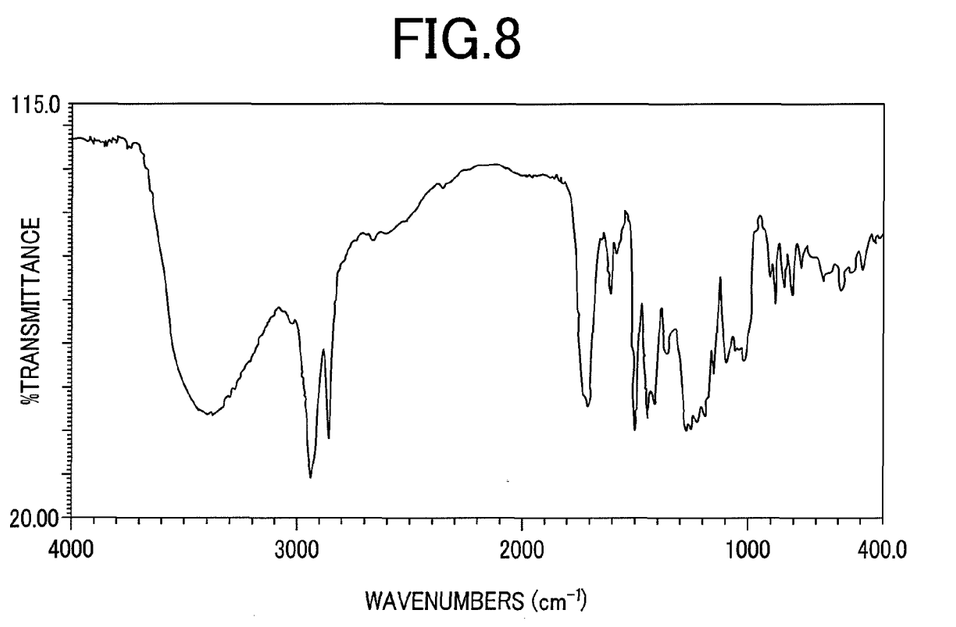
FIG. 8 is a view illustrating an FT-1R spectrum of the material for photoresist A1.

FIG. 8 shows FT-IR spectrum of A1. A major compound of A1 is a composition having the etherification rate of 1, and as a result of the structure analysis by the measurement for Nuclear Overhauser Effect (NOE) of the 2-D NMR and proton NMR, the compound was determined as a mixture of compounds having different etherification positions.

Figure 5:
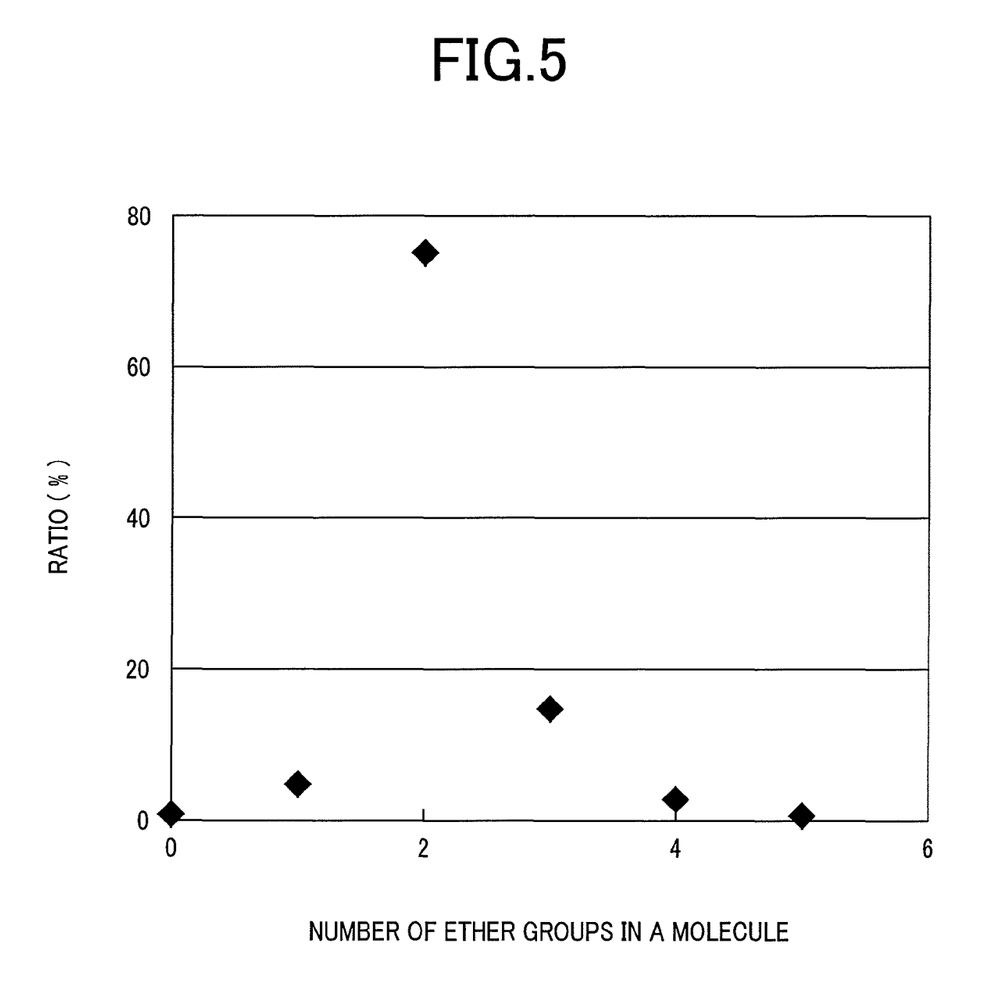
FIG. 5 is a view illustrating a composition distribution of a material for photoresist A2 after column chromatography.
Figure 6:
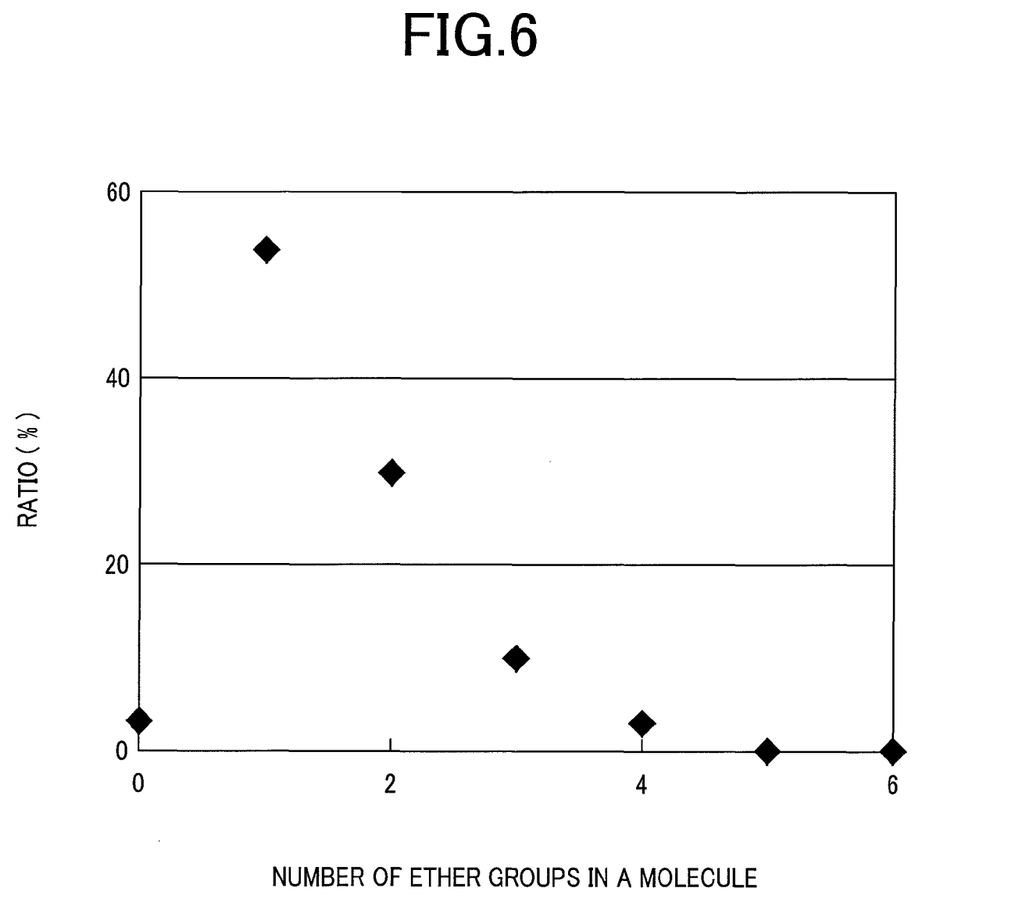
FIG. 6 is a view illustrating a composition distribution of a material for photoresist A3 after column chromatography.

Using the polynuclear phenol X1, conditions for the reaction are changed based on the same synthesizing method for the material for photoresist A1. Then, materials A2 and A3 having a different etherification rate each other were obtained through the separation and purification by the column chromatography and the second step. The composition of A2 is shown in FIG. 5. The etherification rate was 2.2 on average, and specifically, a percentage of compounds having the etherification rate of 0 was 0.9%, a percentage of compounds having the etherification rate of 1 is 5%, a percentage of compounds having the etherification rate of 2 is 75%, a percentage of compounds having the etherification rate of 3 is 15%, and a percentage of compounds having the etherification rate of 4 or more is 4.1%. The composition of A3 is shown in FIG. 6. Namely, the etherification rate was 1.6 on average, and specifically, a percentage of compounds having the etherification rate of 0 was 3%, a percentage of compounds having the etherification rate of 1 is 54%, a percentage of compounds having the etherification rate of 2 was 30%, a percentage of compounds having the etherification rate of 3 was 10%, and a percentage of compounds having the etherification rate of 4 or more was 3%.

Second Embodiment

In this embodiment, a method for synthesizing a material for photoresist (A4) in which δ-hydroxycarboxylic acid is introduced into 3M6C-MBSA (X1).

In the first step (for etherification), polynuclear phenolic compound X1 (15 g) and potassium carbonate were added to acetone (300 ml), and stirred sufficiently. a-bromo-γ-valerolactone (4.0 g) in acetone (50 ml) was added at the room temperature, and the solution was stirred for two hours at the temperature of 45 degrees C. After the reaction was completed, acetone was removed by evapolation under the reduced pressure, water (250 ml) and ethyl acetate (250 ml) were added, and shaken sufficiently in a 1 L separating funnel. The organic layer was recovered, washed with water (300 ml), concentrated, vacuum-dried, and an ether compound of the polynuclear phenolic compound X1 (17 g) was obtained. HPLC analysis was performed to find that etherification rate was 1.2 per 1 molecule on average, and specifically, a percentage of X1 having the etherification rate of 1 was 31%, a percentage of compounds having the etherification rate of 2 was 21%, a percentage of compounds having the etherification rate of 3 was 7%, and a percentage of compounds having the etherification rate of 4 was 2%.

In a step for separation and purification by the column chromatography, the resultant compound in the first step was dissolved into ethyl acetate (20 ml), and the compound was separated by the column chromatography, with silica gel (300 g) as a bonded phase and an eluent including diethyl ether and ethyl acetate as an expansion solvent. An eluate was isolated by 20 ml, and compositions of the recoverable compounds for each fraction were analyzed by HPLC. An appropriate amount of each fraction was recovered, the solvent was removed by concentration and vacuum-dried, and etherified compound of the polynuclear phenol 3M6C-MBSA (5.8 g) was obtained, the composition of which is shown in FIG. 7. The etherification rate was 1 on average, and specifically, a percentage of compounds having the etherification rate of 0 was 0.3%, and a percentage of compounds having the etherification rate of 3 or more was 11%.

In a second step (for alkaline hydrolysis), the ether compound of the polynuclear phenol X1 (5.8 g) having been subjected to separation and refinement by the column chromatography was dissolved into THF (100 ml). 2.38% tetramethyl ammonium hydroxide (TMAH) aqueous solution was added to the resultant solution until pH of the solution was adjusted to about 12. After stirring for 2 hours at the room temperature, THF was removed by evapolation in the depressurized state, ethyl acetate (200 ml) was added and 1% hydrochloric acid aqueous solution until pH was adjusted to about 5 with heavy stirring. The organic layer was washed with water and saturated NaCl aqueous solution, dried with sodium sulfate, and concentrated to obtain the compound A4 (5.2 g) for the photoresist. The number of introduced δ-hydroxycarboxylic acid calculated by HPLC was identical to the etherification rate calculated after the step for the separation and purification, because no ether bond decomposition occurred in this step.

Third Embodiment

In a third embodiment, a method for a pattern forming using the material for photoresist according to the present invention is described.

The material for photoresist A1, 100 weight portions, and 5 weight portions for triphenyl sulfonium triflate acid generator synthesized in the first embodiment were dissolved into weight 500 for propylene glycol monomethyl ether acetate (PGMEA), filtered by the filter having the diameter of 0.20 micrometers to obtain a solution of the photoresist compound.

The photoresist solution was spin-coated to a silicon substrate processed with hexamethyl disilazane, subjected for a thermal processing for two minutes at the temperature of 100°

C., and a resist film having the thickness of 0.20 micrometers was formed. A line and space pattern is drawn on the resist film on the substrate with an electron beam lithography system with the acceleration voltage of 50 kV at an irradiation dose of 10 µC/cm². Then the resist film was subjected to thermal processing for 5 minutes at the temperature of 100° C. to promote lactonization for reducing the solubility of a latent image portion of the resist in an alkaline aqueous solution. After the thermal processing, the resist film with the latent image formed thereon was developed for 60 seconds with a 2.38 weight % aqueous solution of tetramethyl ammonium hydroxide to obtain a negative-tone resist pattern. A cross-sectional form of the line and space pattern with the thickness of 40 nanometers was observed with an scanning electron microscope. As a result, it was recognized that the resist pattern was rectangular and the resolution was high. A quantity of decrease of the film thickness after development is 5 nanometers or less. The line edge roughness (LER) value obtained from a cross-sectional SEM image of the 100 nanometers line and space pattern obtained after development was 3 nanometers.

(Different Material for Photoresist)

The resist composition was prepared in the completely same way excluding the point that A2 was used as a material for the photoresist, and electron beam drawing was performed by the same method and under the same conditions. A 40-nm line and space pattern having an excellent form could be formed at the irradiation dose of 15 µC/cm². The line edge roughness (LER) value was obtained from a length measurement SEM image of the 100 nm line and space pattern obtained after development, and the value was 3 nm.

Also when A3 or A4 was used as a material for photoresist, a 40 nm line and space pattern having an excellent form could be formed in the same way, and the line edge roughness (LER) value was obtained from a length measurement SEM image of the 100 nm line and space pattern obtained after development, and the value was 3 nm.

(Acid Generator)

In the method of forming a photoresist pattern using the A1 above, also when different acid generators (PAG-1, PAG-2, and PAG-4 to PAG-23 shown in FIG. 1A-1L and FIG. 2A-2P), a 40-nm line and space pattern having an excellent form could be formed.

(Solvent)

In the method of forming a photoresist pattern using the A1 above, also when different solvents (such as ethylene dichloride, cyclohexane, cyclopentanone, 2-heptanon, γ-butyrolacton, methyl ethyl ketone, ethylene glycol monomethyl ether, ethylene glycol monomethyl ether, 2-methoxyethyl acetate, ethylene glycol monomethyl ether acetate, propylene glycol monomethyl ether, propylene glycol monomethyl ether acetate, propylene glycol monomethyl ether propionate, toluene, ethyl acetate, methyl lactate, ethyl lactate, methyl methoxypropionate, ethyl methoxypropionate, methyl pyruvate, ethyl pyruvate, propyl pyruvate, N,N-dimethyl formamide, dimethyl sulfoxide, N-methyl pyrrolidone, tetrahydrofuran, γ-butyrolactone), a 50-nm line and space pattern having an excellent form could be formed.

(Surfactant)

In the pattern forming method using the A1 above, also when a fluorine-based or a silicon-based surfactant was added as a solid phase by 0.1% by weight in the resist composition, a 50-nm line and space pattern having an excellent form could be formed.

Sixth Embodiment

In this embodiment, description is provided for a method of forming a photoresist pattern with EUV light using the material for photoresist according to the present invention.

100 weight portions of the material for photoresist (A1) synthesized in the first embodiment, 1.5 weight portions of triphenyl sulfonium naphlate were dissolved in 500 weight portions of 1-methoxy propanol, and the mixture solution was filtered with a 0.10 µm filter to obtain a resist solution.

The resist solution obtained as described above was spin-coated to a silicon substrate processed with hexamethyl disilazane, and the silicon substrate was heated for 2 minutes at 100 degrees C. after application of the resist solution to form a resist film with the thickness of 0.10 µm. After EUV light was irradiated from an EUV exposure tool at the irradiation dose of 10 mJ/cm² to draw a line and space pattern on the resist film. Then the photoresist pattern was subjected to thermal processing for 5 minutes at the temperature of 100 degrees C. to promote the lactonization for reducing solubility of a latent image section of the photoresist pattern in an alkaline aqueous solution. After the postexposure baking processing, the photoresist film with a latent image formed thereon was developed for 40 seconds with an aqueous solution of tetramethyl ammonium hydroxide with the concentration of 2.38% by weight to obtain negative-tone resist patterns.

A cross section of the 30-nm line and space pattern was observed with an scanning electron microscope to confirm that the resist pattern was square and had excellent resolution. The film depletion rate after development was 2 nm or below. The line edge roughness (LER) value obtained from the length measurement SEM image of the 50 nm line and space pattern obtained after development was 2 nm.

Patterns were formed by using A2, A3, and A4 each as a material for photoresist pattern, and 30 nm line and space patterns having an excellent form could be formed at the sensitivity of 9 to 13 µC/cm². The film depletion rate after development was 2 nm or below. The line edge roughness (LER) value obtained from the length measurement SEM image of the 100 nm line and space pattern obtained after development was 2 nm.

(Acid Generator)

In the method of forming a photoresist pattern using the A1 above, also when different acid generators (PAG-1, PAG-2, and PAG-4 to PAG-23 shown in FIG. 1A-1L and FIG. 2A-2P), a 30 nm line and space pattern having an excellent form could be formed.

(Solvent)

In the method of forming a photoresist pattern using the A1 above, also when different solvents (such as ethylene dichloride, cyclohexane, cyclopentanone, 2-heptanone, γ-butyrolactone, methyl ethyl ketone, ethylene glycol monomethyl ether, ethylene glycol monomethylether, 2-methoxyethyl acetate, ethylene glycol monomethyl ether acetate, propylene glycol monomethyl ether, propylene glycol monomethyl ether acetate, propylene glycol monomethyl ether propionate, toluene, ethyl acetate, methyl lactate, ethyl lactate, methyl methoxypropionate, ethyl methoxypropionate, methyl pyruvate, ethyl pyruvate, propyl pyruvate, N,N-dimethyl formamide, dimethyl sulfoxide, N-methyl pyrrolidone, tetrahydrofrane, γ-butyrolactone), a 50 nm line and space pattern having an excellent form could be formed.

(Surfactant)

In the pattern forming method using the A1 above, also when a fluorine-based or a silicon-based surfactant was added as a solid phase by 0.1% by weight in the resist composition, a 30 nm line and space pattern having an excellent form could be formed.

Seventh Embodiment

Using a polynuclear phenol 25X-MBSA as a starting material for etherification of α-bromo-γ-butyrolactone, the first step (etherification), separation and purification by the column chromatography, and the second step were performed line in the first embodiment to obtain a material for photoresist A5. The average etherification ratio was 1.3, and a percentage of compounds with the etherification ratio of zero was 8%, a percentage of compounds with the etherification ratio of 1 was 64%, a percentage of compounds with the etherification ratio of 3 was 8%, and a percentage of compounds with the etherification ratio of 4 was 2%.

A resist liquid was prepared like in the third embodiment and the sixth embodiment excluding the point that the material for photoresist A5 was used, and patterning was performed with an electron beam and EUV light. In any of the cases described above, it was confirmed that the sensitivity was excellent in any case and the resolution of 50 nm or below and LER of 3 nm can be achieved.

Comparative Example 1

A material for photoresist B1 was obtained in the same method as that employed for synthesizing the material for photoresist A in the first embodiment excluding the point that only the separation and purification step by means of the column chromatography was omitted. The composition of the material B1 was checked, before hydrolysis thereof, by HPLC, and a percentage of X1 with the etherification ratio of zero was 37%, a percentage of the compounds with the etherification of 1 was 33%, a percentage of the compounds with the etherification of 2 was 20%, and a percentage of the compounds with the etherification of 4 was 2%. No change was observed in the composition expressed by the etherification ratio even after hydrolysis with an alkaline liquid.

100 weight portion of the material for photoresist (B1), 5 weight portions of triphenyl sulfonium tri-flate were added in 500 weight portions of propylene glycol monomethylether acetate (PEMEA), and the mixture solution was filtered to obtain a solution of a resist composition.

The resist liquid described above was spin-coated onto a silicon substrate processed with hexamethyl disilazane. After application of the resist liquid, the silicon substrate was heated for 2 minutes at 100 degrees C. to form a resist film with the thickness of 0.20 μm. A line and space pattern was drawn on this substrate with an electron beam lithography system operating at the acceleration voltage of 50 kV and at the irradiation dose of 30 μcm². The resist pattern was subjected to thermal processing for 5 minutes at 100 degrees C. to promote lactonization for reducing the solubility of a latent image portion of the resist pattern in an alkaline aqueous solution. After the thermal processing, the resist film with a latent image formed thereon by using an aqueous solution of tetramethyl ammonium hydroxide with the concentration of 2.38% by weight was developed for 60 minutes to obtain a negative-tone resist pattern.

A cross section of the 50 nm line and space pattern was observed with a scanning electron microscope, and it was confirmed that the resist pattern was rectangular and excellent in the resolution. However, the cross-sectional form of the 40 nm line and space pattern was a regularly tapered one, and slight residue was observed in the space portion. A depletion rate after development was 5 nm or below. The line edge roughness (LER) value obtained from the length measurement SEM image of the 100 nm line and space pattern obtained after development was 3.5 nm.

Signs used in the drawings are described below.
700: Materials for photoresist A1
710: Integral curve
720: Spectrum

What is claimed is:

1. A mixture of polynuclear phenol compounds having in one molecule 0 to 6 functional groups which are chemically converted due to actions of an acid with reduced solubility in an alkaline developer, wherein the polynuclear phenol compound is expressed by the following chemical formula (1) and has a structure in which the functional group is bonded to a phenolic hydroxyl group of the polynuclear phenol compounds, and two or more triphenyl methane structures are coupled by a nonconjugate bond, to portions other than the functional group, and the mixture comprises polynuclear phenol compounds with the average number of functional groups of 2.5 or below and includes the polynuclear phenol compounds not having any functional group per molecule by 15% or less in the term of weight ratio, and the polynuclear phenol compounds having 3 or more functional groups per molecule by 40% or less:

Chemical formula (1)

where A in the chemical formula (1) denotes a linear or branched alkyl group, or a cyclic alkyl group having 1 to 10 carbon atoms, where Y in the chemical formula (1) denotes a hydrogen atom or a functional group which is chemically converted with the reduced solubility in an alkaline developer; and each of $R_{11}$, $R_{12}$, $R_{13}$, $R_{14}$, $R_{15}$, $R_{16}$, $R_{17}$, $R_8$, $R_{19}$, $R_{20}$, $R_{21}$, $R_{22}$, $R_{23}$, $R_{24}$, $R_{25}$, $R_{26}$, $R_{27}$, and $R_{11}$ denotes a hydrogen atom or a group selected from the group consisting of alkyl groups or aromatic hydrocarbon groups having 1 to 10 carbon atoms.

2. The mixture of polynuclear phenol compounds according to claim 1, wherein the functional group can be converted from the polar state to the not-polar state, and the polar group is a γ- or δ-hydroxy carboxylic acid, and the not-polar group is a γ- or δ-lactone which is generated when the polar group is etherified in the molecule.

3. The mixture of polynuclear phenol compounds according to claim 2, wherein a functional group bonded to a portion of the phenolic hydroxyl groups of the polynuclear phenol compound has the structure shown by the chemical formula (2) or (3):

Chemical formula (2)

Chemical formula (3)

where in the chemical formulae (2) and (3), each of $R_1$, $R_2$, $R_3$, $R_4$, $R_5$, $R_6$, $R_7$, and $R_8$ denotes a hydrogen atom or an alkyl group having 1 to 10 carbon atoms, and one of $R_1$, $R_2$, $R_3$, $R_4$, $R_5$, $R_6$, $R_7$, and $R_8$ is bonded to a hydroxy group of the polynuclear phenol compound in the form of ether bond.

4. The mixture of polynuclear phenol compounds according to claim 1, wherein the polynuclear phenol compound has a linear or cyclic alkyl group having 1 to 10 carbon atoms at ortho of the phenolic hydroxy group which is chemically converted due to actions of the acid with the solubility in an alkaline developer reduced.

5. The mixture of polynuclear phenol compounds according to claim 1, wherein the polynuclear phenol compound is a compound expressed by the following chemical formula (4):

Chemical formula (4)

where each of $Y_1$ to $Y_6$ in the chemical formula (4) denotes a hydrogen atom or a functional group which is chemically converted due to actions of the acid with the reduced solubility in an alkaline developer.

6. A negative-tone resist composition containing an acid generator which generates an acid when irradiated by a radiation, and also includes a mixture of polynuclear phenol compounds having in one molecule 0 to 6 functional groups which are chemically converted due to actions of an acid with reduced solubility in an alkaline developer,
wherein the polynuclear phenol compound is expressed by the following chemical formula (1) and has a structure in which the functional group is bonded to a phenolic hydroxyl group of the polynuclear phenol compounds, and two or more triphenyl methane structures are coupled by a nonconjugate bond, to portions other than the functional group, and the mixture comprises polynuclear phenol compounds with the average number of functional groups of 2.5 or below and includes the polynuclear phenol compounds not having any functional group per molecule by 15% or less in the term of weight ratio, and the polynuclear phenol compounds having 3 or more functional groups per molecule by 40% or less:

Chemical formula (1)

where A in the chemical formula (1) denotes a linear or branched alkyl group, or a cyclic alkyl group having 1 to 10 carbon atoms, where Y in the chemical formula (1) denotes a hydrogen atom or a functional group which is chemically converted with the reduced solubility in an alkaline developer;

and each of $R_{11}$, $R_{12}$, $R_{13}$, $R_{14}$, $R_{15}$, $R_{16}$, $R_{17}$, $R_8$, $R_{19}$, $R_{20}$, $R_{21}$, $R_{22}$, $R_{23}$, $R_{24}$, $R_{25}$, $R_{26}$, $R_{27}$ and $R_{11}$ denotes a hydrogen atom or a group selected from the group consisting of alkyl groups or aromatic hydrocarbon groups having 1 to 10 carbon atoms.

7. A method of forming a photoresist pattern comprising the steps of:
coating the negative-tone resist composition according to claim 6 to a substrate to obtain a resist layer;
irradiating the resist layer with a radioactive ray; and
developing the resist layer irradiated by the radioactive ray.

* * * * *